US006265169B1

(12) United States Patent
Cortese et al.

(10) Patent No.: US 6,265,169 B1
(45) Date of Patent: Jul. 24, 2001

(54) METHOD BASED ON THE USE OF BACTERIOPHAGES FOR THE DETECTION BIOLOGICAL MOLECULES IN BIOLOGICAL SAMPLES

(75) Inventors: Riccardo Cortese; Paolo Monaci, both of Rome (IT)

(73) Assignee: Istituto di Richerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/424,302
(22) PCT Filed: May 22, 1998
(86) PCT No.: PCT/IT98/00130
 § 371 Date: Feb. 17, 2000
 § 102(e) Date: Feb. 17, 2000
(87) PCT Pub. No.: WO98/53100
 PCT Pub. Date: Nov. 26, 1998

(30) Foreign Application Priority Data

May 22, 1997 (IT) .............................. RM97A0304

(51) Int. Cl.$^7$ ........................................ C12Q 1/68
(52) U.S. Cl. ...................... 435/6; 435/5; 435/6; 435/7.1; 436/518; 436/531; 436/534
(58) Field of Search .................... 435/6, 5, 7.1; 436/518, 436/531, 534

(56) References Cited

U.S. PATENT DOCUMENTS 5,576,197 * 11/1996 Arnold ................................ 435/91.2

FOREIGN PATENT DOCUMENTS

| 0 366 448 | | 5/1990 | (EP) . | |
|---|---|---|---|---|
| 0 544 212 | * | 6/1993 | (EP) | ......................................... 435/6 |
| 0 627 488 | | 12/1994 | (EP) . | |
| WO 85/04189 | | 9/1985 | (WO) . | |
| WO 87/06270 | | 10/1987 | (WO) . | |
| WO 93/15229 | | 8/1993 | (WO) . | |
| WO 93/17129 | | 9/1993 | (WO) . | |
| WO 94/26886 | * | 11/1994 | (WO) | ............................... 435/235.1 |

* cited by examiner

Primary Examiner—W. Gary Jones
Assistant Examiner—Janell E. Taylor
(74) Attorney, Agent, or Firm—Browdy and Neimark

(57) ABSTRACT

The present invention refers to a method that allows the use of filamentous bacteriophages to detect the presence of molecules of interest in biological samples. It consists of a series of combined operations, which are drawn up and defined according to the characteristics of the phages employed. These have, exposed on the surfaces of the capsid, at least one molecule, generally but not exclusively of proteic nature, capable of binding at least one molecule of interest present in the biological sample. Detection of the presence of the molecule takes place, according to the method of the invention, using the association between the molecule exposed on the surfaces of the phage and the genome of the phage itself. The ability to form specific complexes typical of the molecule exposed on the capsid enables formation of phage-molecule of interest complexes, which can be detected by means of amplification of known sequences in the phage DNA. The method according to the invention is extremely sensitive and can be used in particular for diagnostic and prognostic purposes.

14 Claims, 2 Drawing Sheets

METHOD BASED ON THE USE OF BACTERIOPHAGES FOR THE DETECTION BIOLOGICAL MOLECULES IN BIOLOGICAL SAMPLES

CROSS-REFERENCE TO RELATED APPLICATION

The present application is the national stage application under 35 U.S.C. 371 of PCT/IT98/00130, filed May 22, 1998.

BACKGROUND OF THE INVENTION

1. Field of the Invention

The present invention refers to a method for detection of the presence of molecules of interest in biological sources.

2. Description of the Related Art

Providing a method for detecting molecules of interest in biological sources is a need common to many areas of scientific research. In fact, the ability to identify the presence in biological samples of molecules, associated for example with clinical pathologies, has always represented an important objective for research, in particular in the field of medicine.

The bio-medical field is without doubt the main (although not the only) field in which this method is applied. In fact the inventions relating to methods with this purpose have been proposed with the aim of reaching an increasingly high level of sensitivity in detection, in particular at a diagnostic level.

The bio-chemical instrument most frequently used to detect the presence of specific molecules in cell or tissue extracts are antibodies, because of their extreme sensitivity and high binding specificity.

When an interaction with the molecule of interest occurs in these methods, it is highlighted using markers linked to the antibodies themselves, for example fluorescent substances, proteins with enzymatic activity, or radioactive markers.

The detection capacity of these markers has in any case been found to be considerably enhanced by the use of so-called signal amplification methods. These make it possible to obtain a stronger detection signal, for example by joining the marker not to the antibody used for specific recognition (primary antibody), but to a second antibody capable of binding the first one (secondary antibody). A number of methods have been developed using secondary antibodies, to which marker molecules are covalently bonded, for example fluorescent substances such as fluorescein or rhodamin, proteins with enzymatic activity such as alkaline phosphatase or horseradish peroxidase, in case of detection using electron microscope ferritin or colloidal gold spheres are also used.

Alternative amplification systems make use of the high binding affinity of molecules such as Biotin (a small, water-soluble vitamin) and streptavidin (bacterial protein), or those between lecithins (proteins capable of recognising and binding specific saccharide residues) and molecules such as glycoproteins, glycolipids or proteoglycans.

An extremely wide series of variations on this theme is possible, including those allowing creation of a network of markers, capable of considerably amplifying the detection signal. In any case all these methods are connected to the use of antibodies as molecules capable of specific identification of a target molecule, and they also have a sensitivity level that is limited by the concentration of target molecules.

The latter limitation has been overcome by methods drawn up more recently, which are based on the application of PCR (PolymeraseChain Reaction) techniques for this purpose, used here in place of the detection enzymes. These methods, in fact, are again based on the use of monoclonal antibodies against a specific ligand, which in this case, however, are not physically coupled to proteins, but to polynucleotides with a known sequence.

This makes it possible to perform subsequent detection by amplification of the known DNA sequence, which is effectively achieved using a polymerase chain reaction (PCR) (V. Ruzicka et al, 1993; T. Sano et al, 1992; H. Zhou et al, 1993).

This method, known as immuno PCR, makes it virtually possible to detect even a single antibody bound to the target molecule. In spite of the considerable improvement in sensitivity, these methods present a series of problems, among which the direct association of polynucleotides and antibodies, and the resulting high background due to the inevitable interference by the polynucleotide during binding of the antibody to the molecule of interest.

Furthermore, given that the specificity and yield of the amplification reaction depend on the temperature at which the reagents are mixed, it is possible to obtain, if assembly of the PCR reaction takes place at temperatures lower than those considered optimum for hybridisation of the primers, non-specific hybridisation products.

Currently this problem has been solved by addition to the amplification reaction of an essential reagent, only after the system has reached the temperature allowing specific hybridisation of the "Hot Start" primers. This procedure is achieved by mechanically separating a reagent (D. E. Birch et al, 1996), or by using antibodies to block the enzymatic activity of DNA polymerase (J. Cheng et al, 1996).

Recently, a PCR method performed on cells has also been developed, known as in situ PCR (G. J. Nuovo, 1994), in which amplification follows an in situ hybridisation reaction. According to this method, the DNA template and the primers are kept physically separate until the moment of cell lysis, with the advantage of avoiding any non-specific hybridisation reactions (EP 524808 Hoffmann La Roche Inc.).

Furthermore, there are a series of patents all relating to new diagnostic methods that are supposed to overcome many of the problems typical of current methods, and consequently to improve amplification of the response signal. These have as their subject matter various methods, such as the use of PCR associated with the discovery of particular proteins (WO9421676); the use of genetically engineered hybrid enzymes conjugated to ligands, for example epitopes of the virus HIV-1 (WO942636); the use of viral epitopes generated from nucleic acids combined with proteins binding the antigen (WO9406934); the use of parts of viral cDNA, for example taken from HCV, to express a viral epitope connected to a control sequence and a monoclonal antibody directed against the epitope. In the latter case the cDNA region of interest allows cross-reference controls to be carried out between the antibody response and that resulting after hybridisation with the DNA (EP388232).

Another patent, on the other hand, has as its subject the construction of a library of antigenic determinants, obtained by digestion with DNAase-I, of the genome of a virus, for example HIV, which is followed by expression of these fragments obtained by means of a suitable vector, and subsequent selection of said expression products by the use of antibodies (EP373070).

SUMMARY OF THE INVENTION

Object of the invention is a method for detection of the presence of a molecule of interest in a biological sample, comprising a combination of the following operations:

a) immobilising the molecules of interest without destroying the ability to interact with the molecules exposed on the surfaces of the phage;

b) causing a molecule of interest, immobilised as above, to bind specifically with at least one of the recombinant filamentous bacteriophages, which have internally a single-strand DNA molecule whose sequence is at least partially known, and exposing on the surfaces of the capsid at least one molecule capable of binding specifically to at least one molecule of interest present in the biological sample;

c) separating the molecule-bacteriophage complexes obtained in this manner from the reaction mixture;

d) washing to remove the complexes generated by non-specific interaction between molecule and bacteriophage;

e) adding the reagents to carry out the operation described under g) below;

f) lysing the proteins forming the protein capsid of the bacteriophages selected in this way;

g) amplifying the DNA obtained as above by polymerase chain reaction (PCR);

h) detecting the DNA amplified as above.

A first advantage of said method is the fact that it is extremely versatile, as it can be used in widely differing situations and for widely differing purposes, according to methods that enable various problems present in the state of the art to be overcome.

The method according to the invention does not in fact presuppose the production of specific antibodies, but the use of recombinant filamentous phages exhibiting onto the capsid any molecule capable of interacting with the molecule of interest in the sample to be examined.

It also allows, when a phage exhibiting a suitable molecule is available, detection of the presence of any type of molecule of interest (not merely amino acids), even if the molecule in question is present in infinitesimal amounts, in biological samples of various origin (not only in samples taken from the human body or from the body of animals, but also in samples of other types, for example water, drinks or food substances). Combination of the operations forming the subject of the invention is also articulated so as to eliminate the risk of non-specific association between DNA and reagents and the consequent background, which can compromise the clarity of the result.

These advantages are a consequence of the fact that the DNA used to detect by PCR is not directly exposed to the reagents, but is contained inside the recombinant phages employed.

The presence of the proteic capsid wrapping actually prevents the DNA used for subsequent detection from interfering during the binding reaction between the ligand molecule (the one exposed on the capsid) and the receptor molecule (the one of interest in the sample).

Following this, after interaction between the ligand molecule and the receptor molecule, suitable washing operations are carried out to eliminate the phages that have not been bound by specific interaction to the receptor. Finally, the nucleotide sequences of the phage DNA are amplified by adding the necessary reagents according to a process that avoids the insurgence of non-specificity. In fact, the DNA to be amplified remains protected during the initial stages by the proteins of the phage capsid, which are only denatured at the moment in which the polymerisation reaction starts.

A further advantage derives from the fact that the basic recombinant phagemid, used to construct the receptor phages, is essentially secreted by *E. coli* as a particle containing single-strand DNA. It is, in fact, known from the state of the art that the use of PCR on a single-stranded DNA template gives better results than that carried out on double-strand DNA.

In particular, in advantageous embodiments of the present invention, the operation indicated under f) is performed at a temperature at which denaturation of the DNA takes place, whereby a "Hot Start" for the PCR of the operation under g) is achieved; the molecules of interest are antibodies; the molecules of interest are immobilised on a solid phase, preferably by passive adsorption in particular by the use of antibodies specific to the molecules themselves, or by use of bacteria or of at least one of the bacterial proteins, selected from the group comprising protein A of *Staphylococcus aureus*, protein G of group C Streptococci and any other bacterial protein capable of binding animal immunoglobulins.

In further preferred embodiments, the bacteriophages exhibit on the surfaces of the capsid one or more of: viral antigens, parts thereof or oligopeptides capable of mimicking the effects of their presence in the biological sample; auto-antigens, parts thereof or oligopeptides capable of mimicking the effects of their presence in the biological sample; allergens, parts thereof or oligopeptides capable of mimicking the effects of their presence in the biological sample; cell membrane receptors, parts of said receptors or oligopeptides capable of mimicking the biological activity thereof; specific cell membrane receptors or peptides deriving therefrom; ligands of an amino acid nature whose receptor is presumed to be present in the fluids to be tested.

The invention will be further clarified with reference to the annexed figures.

DETAILED DESCRIPTION OF THE INVENTION

Figure 1:
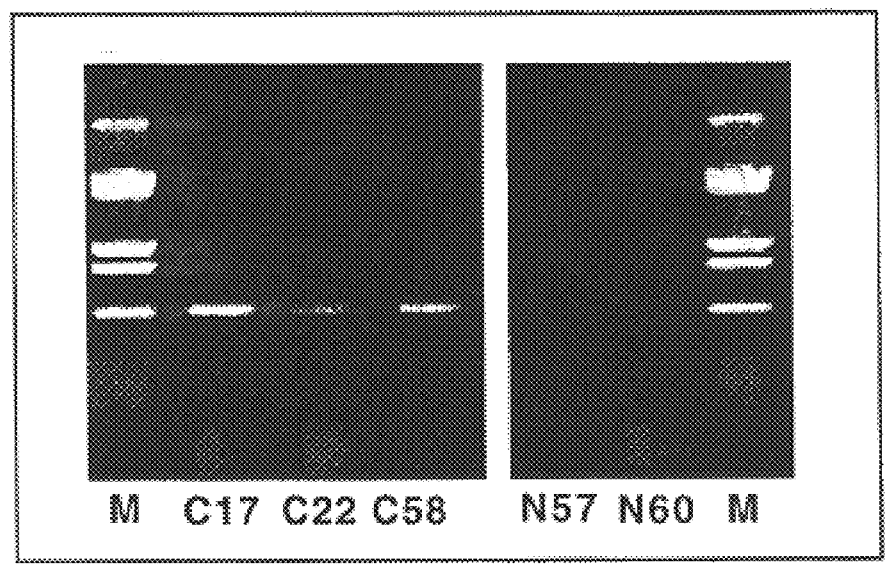
FIG. 1 shows the result of amplification of the DNA of a phage P787, exhibiting on the surface of the capsid a peptide capable of binding anti-HCV antibodies. Visualisation is by UV fluorescence on agarose gel containing ethidium bromide. M is a reference to molecular weights obtained by hydrolysing the plasmid DNA pUC19 with the restriction enzyme Hinf I.

The subject matter of the present invention is a method for the determination and measurement of the presence of certain molecules of interest, also indicated in this context as receptor molecules, on the basis of their ability to be specifically recognised at least by a certain molecule, here indicated as the ligand molecule, which is exposed on the phage capsid.

It is necessary to underline how in the present description the concepts of ligand molecule and receptor molecule are strictly interdependent, and strictly bound to the specific working context. As a result of this, a molecule exposed on the surface of the capsid is defined "ligand" solely on the basis of its ability to specifically bind to the molecule presumed to be present in the sample, the presence or concentration of which is to be measured, which is therefore defined "receptor", and vice versa.

In the present invention, any molecule obtained from sources such as biological fluids, surfaces of cells or tissues, is considered to be a "receptor" if its presence can be identified by means of interaction with a specific "ligand" as defined above. For example, antibodies capable of recognising clearly identified antigens (such as viral antigens, tumoural antigens or antigens present in normal tissues), or antigens whose precise molecular nature has not yet been identified, belong to the category of "ligands", although they are not alone in that category. In this case, these antigens will be considered to be "receptors". These definitions are connected, for example, to the case in which the presence and/or concentration of these antigens in the biological fluids or on the surfaces of cells and tissues under examination is an indication with diagnostic value. However, in accordance with the method according to the present invention the antigens themselves can be used as "ligands" in the case that the receptor molecule of interest, the presence or concentration of which it is necessary to determine, is made up of antibodies.

In the same way it is possible to consider "receptors", if of interest, even specific receptors present on the membrane of single cells or of the cells in tissues, along with the soluble receptors present in biological fluids, which will be detected in this case by the molecules capable of binding with them specifically, acting as "ligands". Naturally it is possible to invert the relationship when the molecules of interest are no longer made up of membrane receptors (which in this case will act as "ligands"), but of their specific ligands (which in this case will be considered "receptors").

It can thus be understood that any molecule whose presence in the sample under examination is considered to have a diagnostic and/or prognostic value (after having ascertained its association with the appearance of a specific pathology), or is of interest for whatever purpose, can be included in the category "receptors".

The many applications of this method are quite evident, particularly in the medical and veterinary field, but also in other fields, for example food and the environment.

This method has been drawn up following verification by the inventors of the possibility of using filamentous bacteriophages, either recombinant or non-recombinant, to detect interaction between a "ligand" and a receptor molecule present in a sample, even at extremely low concentrations, by amplification of specific nucleotide sequences present in the phage genome and physically or genetically associated with the "ligand".

In brief, the method according to the invention can be applied every time it is possible to identify:

A) a receptor molecule or a homogeneous class of "receptors" forming a group, the presence of which in biological fluids or on the surfaces of cells or tissues is correlated with a certain pathology or is in any case of considerable interest, for example for diagnostic purposes;

B) a "ligand" or a class of "ligands", for example of polypeptide type, whose structure allows them to be exposed on the capsid of bacteriophages, preserving the ability to bind specifically to the receptor molecule.

The subject matter of the present invention is therefore a method based essentially on the following operations:

a) immobilising the molecules of interest without destroying the ability to interact with the molecules exposed on the surfaces of the phage;

b) causing a molecule of interest, immobilised as above, to bind specifically with at least one of the recombinant filamentous bacteriophages, which have internally a single-strand DNA molecule whose sequence is at least partially known, and exposing on the surfaces of the capsid at least one molecule capable of binding specifically to at least one molecule of interest present in the biological sample;

c) separating the molecule-bacteriophage complexes obtained in this manner from the reaction mixture;

d) washing to remove the complexes generated by non-specific interaction between molecule and bacteriophage;

e) adding the reagents to carry out the operation described under g) below;

f) lysing the proteins forming the protein capsid of the bacteriophages selected in this way;

g) amplifying the DNA obtained as above by polymerase chain reaction (PCR);

h) detecting the DNA amplified as above, for example using conventional methods.

The methods for detecting the amplified DNA can be for example electrophoresis on agarose gel in the presence of ethidium bromide, capillary electrophoresis, hybridisation to specific radioactively marked or luminescent probes.

In particular, the operation indicated under g), that is to say, amplification of the phage DNA, is carried out using PCR techniques, using a pair of oligonucleotides of which at least one is complementary to a known sequence of the phage DNA. Furthermore, it has been found that using a protocol for lysis of the phage capsid proteins at the temperature in which denaturation of the DNA takes place, which usually falls within the range of 93–96° C., contact between primers and DNA template takes place at the same temperature, and thus a "Hot Start" is obtained for the PCR, with the consequent virtual elimination of non-specific reaction products.

An important application for this method is when the molecules of interest are antibodies.

A further specific application is when immobilisation of the molecules of interest is carried out in the solid phase, and in this case when it is in turn achieved by passive adsorption and/or using antibodies specific for the molecules themselves.

In any event, immobilisation can also be achieved by use of bacteria or of at least one of the bacterial proteins selected from the group comprising protein A of *Staphylococcus aureus,* protein G of group C Streptococci and any other bacterial protein capable of binding animal immunoglobulins.

Further applications of the method, of particular interest, are those in which the bacteriophages used exhibit on the surfaces of the capsid viral antigens, auto-antigens (antigens that can be present in the animal which is the source of the biological fluids), allergens, cell membrane receptors, parts of said molecules or oligopeptides capable of mimicking the presence thereof in the biological fluids under examination, as well as specific cell membrane receptors or peptides deriving therefrom, or ligands of amino acid type whose receptor is present in the fluids to be tested.

Among the fundamental aspects of this method is first of all the fact that the instruments used for detection are always filamentous bacteriophages, generally of recombinant type M13, f1 or fd, which make it possible to expose on the surfaces of the capsid one or more molecules, preferably of amino acid type, which act as "ligands", capable of interacting specifically with the "receptor" that is to be tested. This forms a first element of originality, given that there is no longer direct use of ligand molecules, but of phages containing suitably selected natural "ligands", their parts or mimes.

The present invention distinguishes itself from other detection methods described in the past, such as immuno-PCR, in which an antibody is artificially bound to a polynucleotide molecule with a known sequence used as a probe, in the very fact that in this invention the genetic information contained inside the phage is used to determine the presence of a molecule of interest.

Furthermore, the ability to use different phages simultaneously make it possible to detect simultaneously different parts of a molecule of interest, or even a number of molecules of interest.

However, the main characteristic is above all the association of the "ligand" exposed on the surfaces of the phage and the phage DNA, used for detection by PCR. This can be made up of the genetic information coding for the "ligand", but also more generally of any nucleotide sequence in the phage genome.

As a result of this the method of the invention it also makes possible the selection of nucleotide sequences associated with the "ligand" to be used for detection, so as to increase the specificity and decrease the amplification reaction time. In effect, to achieve a PCR reaction, the sequence of the oligonucleotide primers, the duration and the temperature at which each incubation takes place, and the number of cycles in each reaction, can be pre-selected at this time so as to obtain extremely rapid and highly specific amplification.

In effect, by its nature, the genetic information present inside the phage and used for detection is particularly prone to be amplified using current PCR methods, which make it possible to highlight the presence of even a single DNA molecule in the reaction tube. The sensitivity that can be obtained using the polymerase chain reaction cannot easily be reached using other detection methods currently in use.

A further advantage resulting from this is closely connected to the fact that the oligonucleotide probes used for amplification can be designed so as to give specific amplification of a particular sequence present in a phage, even in the presence of the DNA from other phages that do not include it. For example it is possible to design the probes so as to amplify only the DNA of phages containing a specific insert (for example the one coding for the molecule that acts as a "ligand" when exposed on the capsid), even in the presence of the DNA of phages that do not contain this insert, or that contain inserts with a different sequence. The most direct consequence of this is that it is possible to react the receptor molecule (or the receptor molecules) under examination with a mixture of different phages, and identify the bond with each single type of phage even in the presence of the others.

Furthermore, the fact that the DNA is contained inside the proteic capsid enables one of the limitations in detection specificity typical of PCR methods to be overcome. This limitation is the need to place the DNA template in contact with the amplification probes at a relatively low temperature, according to the sequence of the two primers. When the temperature is raised to start the first amplification cycle, part of the DNA remains complexed to the probe and this results in a non-specific elongation of the probe itself on the DNA template. Various methods have been proposed to remedy this problem (4, 5). The method of the present invention, as mentioned above, enables the problem to be solved brilliantly, making use of the fact that a naturally encapsidated DNA is used, which is therefore protected from contact with the specific probes until the time of lysis of the capsid. In this regard, an extremely high specificity can be obtained merely by perfecting the method and using a thermal lysis protocol that allows contact between the DNA and the specific probe only at high temperature.

In this manner, which is achieved in the embodiment rather simply and is extremely practical, it is possible to obtain what in technical terms is known as a "Hot Start" for the PCR.

Up to this point a general description has been given of the present invention. With the aid of the following examples, a more detailed description of specific embodiments will now be given, with the aim of giving a clearer understanding of the objects, characteristics, advantages and operating methods of the invention. These examples are merely illustrative, and in no way limit the scope of the present invention, which is defined in the enclosed claims.

EXAMPLES

Example 1

Method for Detection, in the Serum of Patients, of the Presence of Antibodies Specific for the Antigens of Human Hepatitis C Virus (HCV)

The following method was used according to the invention:

Amounts of human goat-anti-IgG immunoglobins, specific for the Fc portion, were absorbed in the wells of a polycarbonate plate made up of 96 wells, currently in use for PCR methods (Thermowell-II™ type 6509 produced by Costar). After incubation the plate was washed with a saline phosphate buffer, and the residual absorption sites were blocked by incubation in a buffer in which powdered skimmed milk was re-suspended (as described in the literature). The following were dispensed into the wells on the plate prepared in this way: 1) amounts of the human serum being tested, diluted to various levels; in this example the human serum types C17 and C22 from patients infected with HCV and containing anti-HCV antibodies was used. N57 and N60 were serum types obtained from apparently healthy individuals in which no anti-HCV antibodies were found. Amounts of these serums were mixed with a phage of non-recombinant type, which acts as a non-specific carrier. A recombinant phage 2A was also added, that can be amplified in the PCR reaction but that does not exhibit the specific ligand on the capsid, in this example peptides capable of binding human anti-HCV antibodies; and alternatively 2B the HCV-specific phage P787.

After incubation at 37° for 90 minutes, the plate was emptied and washed with phosphate buffer to remove all the recombinant phages that were not specifically bound. A mixture was then added to each well, containing the DNA probes specific for amplification, the polymerase Taq, triphosphate dioxynucleotides, in a buffer suitable for the PCR reaction.

The plate was transferred to a thermal incubator for PCR and the process continued with reaction cycles that started with heating for 5 minutes at 95° C. This passage is particularly important because it is only at this temperature that lysis of the phage proteins takes place, and consequently contact of the specific probes with the DNA to be amplified. The PCR reaction this starts at high temperature (hot start) and continues with 25 cycles of 10 seconds at 94° C. and 10 seconds at 72° C. The reaction terminates with incubation at 72° C. for 2 minutes.

The DNA of phage P787 amplified in this way is highlighted by electrophoresis on agarose gel containing ethidium bromide, as shown in the specific example of FIG. 1.

Example 2
Use of a Composition of Phages to Diagnose the Presence of anti-HCV Antibodies in the Serum of Patients A composition of a number of specifically selected phages, each of which mimics different proteic regions of the human hepatitis C virus, was used to diagnose the presence of anti-HCV antibodies in a serum. As the phages can be distinguished according to the sequence they carry, but also, more simply, by the length of the insert, it is possible to observe amplification of DNA fragments of different lengths on the agarose gel, according to the dimensions of the phage DNA insert.

In this example it is shown how, using a mixture of phages, it is possible to obtain a response on agarose gel as described in example 1. The example shows that a mixture of phages is more predictive than use of a single phage.

Figure 2:
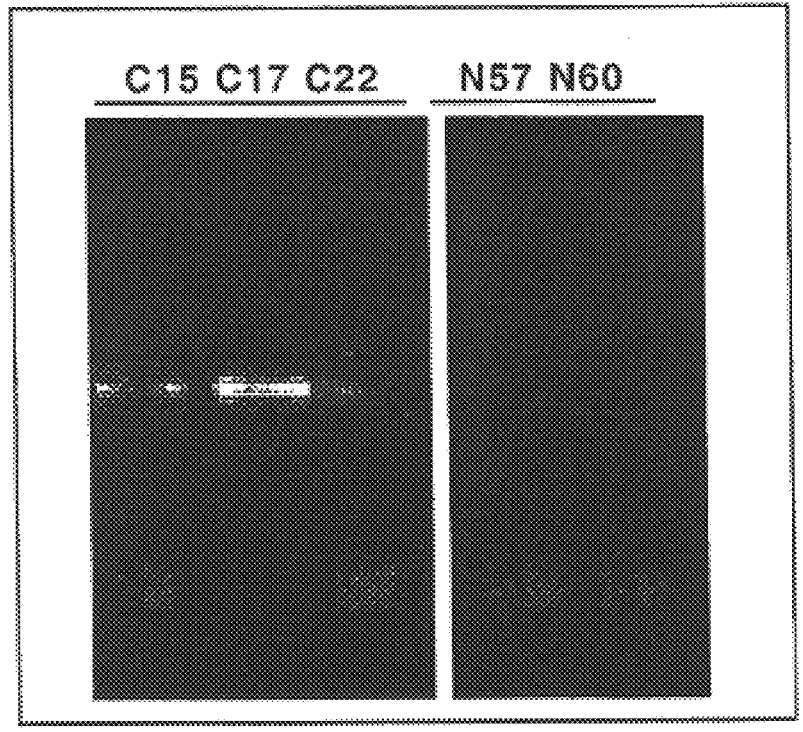
FIG. 2 shows the result of amplification of the DNA of a phage mix after incubation with C17 and C22 serum from patients whose serum contains anti-HCV antibodies. Visualisation is by UV fluorescence on agarose gel containing ethidium bromide. PC89 is the non-recombinant phage with which the phage library was constructed, used here as a negative control.
Figure 3:
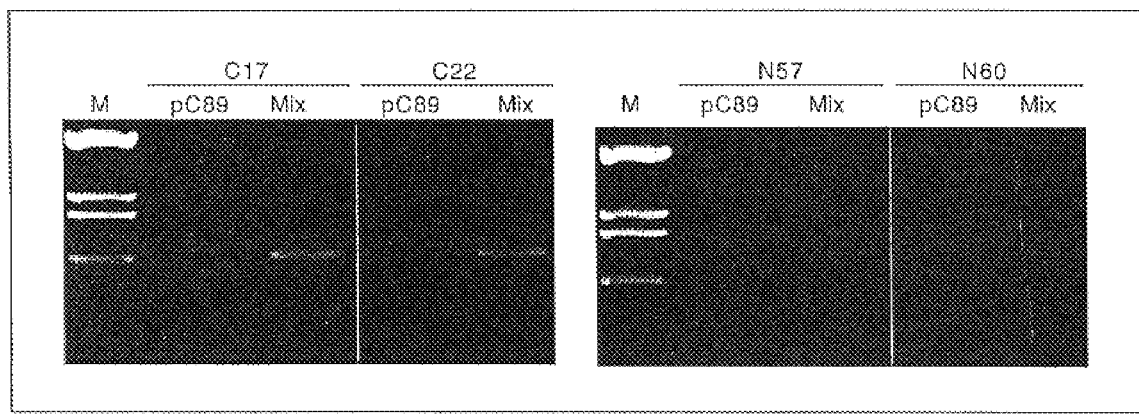
FIG. 3 shows the result of amplification of the DNA of the same phage mix used in FIG. 2, after incubation with N57 and N60 serum from two volunteers whose serum does not contain anti-HCV antibodies, and who are therefore considered negative controls. Visualisation is by UV fluorescence on agarose gel containing ethidium bromide. PC89 is a negative control phage described above in example 1. M is a reference to molecular weights obtained by hydrolysing the plasmid DNA pUC19 with the restriction enzyme Hinf I.

It is surprising that in a serum it is possible to identify antibodies for different antigens, and that the amplification response is specific. The result shown in FIG. 2 and FIG. 3 consists however of a response that can be analysed by electrophoresis as described above for example 1.

Example 3
Method for Detection in vitro of Human Anti-IL-6 Antibodies

A method is described in which the receptor for IL-6 is immobilised on a plate and phages expressing IL-6 are used to detect the presence thereof in extra-cellular culture mediums.

The human cDNA coding for hIL-6 was fused to the amino-terminal end of gene III of a phagemid obtained from M13 as described in the literature. The recombinant hIL-6/M13-pIII phage can be used to detect the presence of the human interleukin 6 receptor. In the art a description has already been given of how it is possible to select a phage expressing hIL-6 that is capable of binding in vitro both hIL-6/R and anti-hIL-6 antibodies as described in the literature. We have proved that recognition is possible and more effective if the method described in the present invention is used.

On a solid support, for example a plastic bead, 1 $\mu$g of monoclonal anti-hIL-6 antibodies were fixed in 10 mM of NaHCO3 at pH 9.2 for incubation at 4° C. overnight. After blocking in 1 ml of TBS/6% BSA for 4 hours at 4° C. the beads were incubated overnight with hIL-6 at 4° C. The beads were twice subjected to washing with 2 ml of TBST followed by incubation for 1 hour in 1 ml of TBST/0.1% BSA at 20° C. Subsequently the phages were eluted in 500 $\mu$l of 100 mM glycine HCl pH 2.2 and the eluate was neutralised with 3M Tris HCl pH 8.9. The phages bound to the antibodies can be detected by PCR, as described in the invention.

Example 4
Method for Detection of the Soluble Form of the Human IL-6 Receptor within a Culture of Engineered CHO Cells A method is described in which the human IL-6 receptor, expressed in engineered ovary carcinoma cells, is detected according to the method described in the present invention and if possible quantified using phages capable of expressing IL-6 or superantagonists of IL-6.

A CHO cell line (CsRh14) is capable of secreting a soluble form of the interleukin 6 receptor (ref). Using 100 $\mu$l of tosyl-activated Dynabeads M450 (unipath) a concentrated form was prepared, using a magnetic particle concentrator, washed with 50 mM sodium borate at pH 9.5 and incubating for 24 hours at 25° C. in 400 $\mu$l of the same buffer containing 15 $\mu$g of monoclonal anti-hIL-6R$\alpha$ antibodies. After saturating passage in TBS/0.1%BSA for 12 hours at 4° C., the beads were incubated for 4 hours at 25° C. with 400 $\mu$l of conditioned medium containing no serum, obtained from the line CsRh14, containing 250 ng of shIL-6R$\alpha$. After washing several times the beads to which the shIL-6R$\alpha$ had been bound were incubated with the phages expressing hIL-6 (in a ratio of 1:4) for 16 hours at 4° C. The reaction volume was brought up to 1 ml by adding an appropriate amount of TBS/0.1%BSA. The beads were washed 3 with 1 ml of TBST and the phages eluted in 400 ml of 100 mM citrate buffer at pH 3.2. After neutralisation with 3M Tris CHl pH 8.9 the bound phages were detected by PCR amplification, in accordance with the nature of the present invention.

REFERENCES

1. V. Ruzicka, W. Marz, A. Russ and W. Gross: 1993 260, 698–699.
2. T. Sano, C. L. Smith, C. R. Cantor: 1992 Science 258, 120–122.
3. H. Zhou, R. J. Fischer and T. S. Papas: 1993 Nucl. Ac. Res. 21, 6038–3039.
4. D. E. Birch, L. Kolmodin, J. Wong, G. A. Zangenberg and M. A. Zoccoli: 1996 Nature 381, 445–446.
5. J. Cheng, M. A. Shoffner, G. E. Hvichia, L. J. Kricka and P. Wilding: 1996 Nucl. Ac. Res. 24, 380–385.
6. G. J. Nuovo PCR in situ hybridization, Protocols and applications. Rower Press 1994.

What is claimed is:

1. A method for detecting the presence of a molecule of interest in a biological samples, comprising a combination of the following operations:

a) immobilising molecules of interest without destroying their ability to specifically interact with molecules exposed on the surfaces of a recombinant filamentous bacteriophage, which bacteriophage contains a single-strand DNA molecule whose sequence is at least partially known;

b) causing an immobilised molecule of interest to bind specifically with at least one of the molecules exposed on the surface of at least one of a plurality of recombinant filamentous bacteriophages in a reaction mixture to form an immobilised complex between said molecule of interest and said at least one bacteriophage;

c) separating said immobilised complex from the reaction mixture;

d) washing to remove any complexes generated by non-specific interaction between said molecule of interest and bacteriophage;

e) adding the reagents to carry out the operation described under g);

f) lysing the proteins forming the protein capsid of said bacteriophage of said immobilised complex;

g) amplifying the DNA obtained from lysing said bacteriophage;

h) detecting the amplified DNA.

2. The method according to claim 1, in which operation f) is performed at a temperature at which denaturation of the DNA takes place, whereby a "Hot Start" for the PCR of the operation under g) is achieved.

3. The method according to claim 1, in which the molecule of interest is an antibody.

4. The method according to claims 1, in which the molecule of interest is immobilised on a solid phase.

5. The method according to claim 4, in which immobilisation on the solid phase of the molecule of interest takes place by passive adsorption.

6. The method according to claim 4, in which immobilisation of the molecule of interest on the solid phase takes place by the use of antibodies specific to the molecule of interest.

7. The method according to claim 3, in which immobilisation of the molecules in the solid phase takes place by use of bacteria or of at least one of the bacterial proteins, selected from the group consisting of protein A of *Staphylococcus aureus,* protein G of group C Streptococci and any other bacterial protein capable of binding animal immunoglobulins.

8. The method according to claim 1, in which the bacteriophage exhibits on the surfaces of the capsid viral antigens, parts thereof or oligopeptides capable of mimicking the effects of their presence in the biological sample.

9. The method according to claims 1, in which the bacteriophage exhibits on the surfaces of the capsid autoantigens, parts thereof or oligopeptides capable of mimicking the effects of their presence in the biological sample.

10. The method according to claim 1, in which the bacteriophage exhibits on the surfaces of the capsid allergens, parts thereof or oligopeptides capable of mimicking the effects of their presence in the biological sample.

11. The method according to claim 1, in which the bacteriophage exhibits on the surfaces of the capsid cell membrane receptors, parts of said receptors or oligopeptides capable of mimicking the biological activity thereof.

12. The method according to claim 1, in which the bacteriophage exhibits on the surfaces of the capsid specific cell membrane receptors or peptides deriving therefrom.

13. The method according to claim 1, in which the bacteriophage exhibits on the surfaces of the capsid ligands of an amino acid nature whose receptor is presumed to be present in the biological sample tested.

14. The method according to claim 1, in which the bacteriophage exhibits jointly on the surfaces of the capsid two or more molecules selected from the group consisting of: viral antigens, parts thereof or oligopeptides capable of mimicking the effects of their presence in the biological sample; auto antigens, parts thereof or oligopeptides capable of mimicking the effects of their presence in the biological sample; allergens, parts thereof or oligopeptides capable of mimicking the effects of their presence in the biological sample; cell membrane receptors, parts of said receptors or oligopeptides capable of mimicking the biological activity thereof; specific cell membrane receptors or peptides deriving therefrom; ligands of an amino acid nature whose receptors is presumed to be present in the biological sample.

* * * * *